(12) United States Patent
Ekwuribe et al.

(10) Patent No.: US 6,458,776 B1
(45) Date of Patent: Oct. 1, 2002

(54) 5-ASA DERIVATIVES HAVING ANTI-INFLAMMATORY AND ANTIBIOTIC ACTIVITY AND METHODS OF TREATING DISEASES THEREWITH

(75) Inventors: Nnochiri Nkem Ekwuribe, Cary, NC (US); Jennifer A. Riggs-Sauthier, Raleigh, NC (US); Elizabeth Malson, Burbank, CA (US)

(73) Assignee: Nobex Corporation, Durham, NC (US)

( * ) Notice: Subject to any disclaimer, the term of this patent is extended or adjusted under 35 U.S.C. 154(b) by 0 days.

(21) Appl. No.: 09/942,510

(22) Filed: Aug. 29, 2001

Related U.S. Application Data
(60) Provisional application No. 60/228,682, filed on Aug. 29, 2000.

(51) Int. Cl.[7] .................. A61K 31/655; C07C 311/39; C07C 311/51
(52) U.S. Cl. ........................................ 514/150; 534/660
(58) Field of Search ............................ 514/150; 534/660

(56) References Cited

U.S. PATENT DOCUMENTS

| | | | |
|---|---|---|---|
| 2,270,676 A | 1/1942 | Behnisch et al. | 562/65 |
| 4,412,992 A | 11/1983 | Chan | 514/150 |
| 6,197,341 B1 * | 3/2001 | Friess et al. | 424/474 |

OTHER PUBLICATIONS

Jain et al., "Studies in Sulphanilamides. Part XIII. Reaction with Dicarboxylic Acids. Some New $N^1$– and $N^4$–Acyl and Heterocyclic Derivatives," *J. Indian Chem. Soc.*, 24: 173–176 (1947).

Kimura et al., "Determination of the Active Moiety of BX661A, a New Therapeutic Agent for Ulcerative Colitis, by Studying Its Therapeutic Effects on Ulcerative Colitis Induced by Dextran Sulfate Sodium in Rats," *Drug Res.*, 48(II)(11): 1091–1096 (1998).

E. Hackmann & P.C. Ferreira, "Nuovi Azoderivati Solfammidici," *Boll. Chim. Farm.*, 114(9): 501–508 (1975).

Osman et al., "Synthesis of Sulfanilamido–Naphthoquinones as Potential Antituberculous Agents," *Journal of Pharmaceutical Sciences*, 72(1): 68–71 (1983).

Frommel et al., "La Paraminobenzolsulfonesuccinylimide, Sulfamide Soluble Neutre et Injectable," *Helv. Physiol. Acta.*, 3: 261–268 (1945).

International Search Report corresponding to PCT/US 01/41910; date of mailing: Dec. 27, 2001.

* cited by examiner

*Primary Examiner*—Fiona T. Powers
(74) *Attorney, Agent, or Firm*—Myers Bigel Sibley & Sajovec, P.A.

(57) ABSTRACT

Compounds are disclosed represented by the following formula:

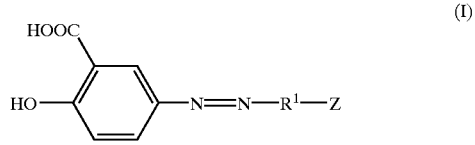

(I)

where $R^1$ is a substituted or unsubstituted phenyl group, and where Z is selected such that a compound, $Z\text{-}R^1\text{-}NH_2$, formed by cleavage of the azo bond is a non-absorbable antibiotic; or an ester or pharmacologically acceptable salt of the compound of Formula I. Compounds of the present invention may be utilized for the prophylaxis or treatment of various diseases including, but not limited to, intestinal diseases such as inflammatory bowel disease and/or traveler's diarrhea, liver diseases such as hepatic encephalopathy, and/or diseases treatable by a non-absorbable antibiotic.

60 Claims, 2 Drawing Sheets

5-ASA DERIVATIVES HAVING ANTI-INFLAMMATORY AND ANTIBIOTIC ACTIVITY AND METHODS OF TREATING DISEASES THEREWITH

RELATED APPLICATION

This application claims the benefit of United States Provisional Application No. 60/228,682, filed Aug. 29, 2000, the disclosure of which is incorporated herein by reference in its entirety.

FIELD OF THE INVENTION

The present invention relates to 5-ASA derivatives and methods of treating diseases therewith.

BACKGROUND OF THE INVENTION

Many people suffer from inflammatory bowel disease (IBD). TRD is a generic term used to refer to two inflammatory diseases, ulcerative colitis and Crohn's disease. Ulcerative colitis is a chronic inflammatory disease of unknown etiology that affects various portions of the gastrointestinal (GI) tract, particularly the lower GI tract, and more particularly the colon and/or rectum. Crohn's disease is a serious inflammatory disease of the GI tract. It predominates in the intestine (ileum) and the large intestine (colon). Various medications are being used to treat inflammatory bowel disease.

It is known to use mesalamine, 5-aminosalicylic acid (5-ASA) to treat ulcerative colitis. While mesalamine may be active in treating ulcerative colitis, it may be absorbed as it passes through the GI tract. This absorption may adversely affect the amount of mesalamine that reaches the lower GI tract, particularly the colon and rectum.

Various mesalamine formulations have been introduced in an attempt to protect mesalamine as it passes through the gut and the upper GI tract. One such formulation is a delayed-release formulation that relies on a pH-sensitive coating surrounding the mesalamine. The coating allows the mesalamine to pass through the gut and upper GI tract without being absorbed so that the mesalamine reaches the target (i.e. the lower GI tract, particularly the colon and/or rectum) intact. In another formulation, mesalamine microspheres surround a mesalamine core. This formulation releases mesalamine throughout the GI tract, rather than targeting the colon specifically. It may be difficult to predict the bioavailability of the various mesalamine formulations when administered to a wide variety of individuals. As a result, it may be difficult to determine the proper dosage for a given individual.

It is also known to use sulfasalazine having the following formula to treat ulcerative colitis.

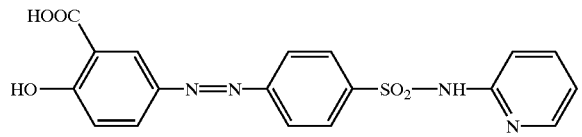

However, sulfasalazine is metabolized in the body to form mesalamine (5-aminosalicylic acid (5-ASA)) and sulfapyridine. Several adverse side affects have been noted from the use of sulfasalazine including nausea, vomiting, abdominal discomfort, and headache to name just a few. These adverse side effects are usually attributed to the activity of sulfapyridine in the GI tract, as well as that absorbed into the system.

U.S. Pat. No. 4,412,992 to Chan proposes mesalamine derivatives. Unlike sulfasalazine, the breakdown of these compounds in the intestinal tract may not give rise to undesirable metabolic products. In fact, the non-mesalamine metabolic products may be innocuous.

It is also known to use olsalazine having the following formula to treat ulcerative colitis.

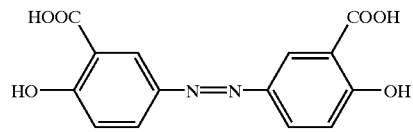

In addition to being relatively expensive to make, olsalazine may have adverse side effects including diarrhea.

It is also known to use azathioprine (6-(1-methyl-4-nitoimidazol-5-ylthio)purine) in the treatment of inflammatory bowel disease. Azathioprine has the following chemical structure:

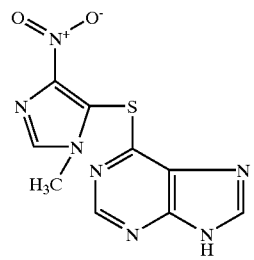

It is also known to use 6-mercaptopurine, a metabolite of azathioprine, to treat inflammatory bowel disease. 6-mercaptopurine has the following chemical structure:

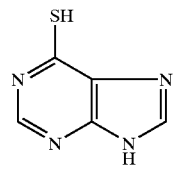

Methotrexate (L4amino-$N^{10}$-methylpteroyl-glutamic acid) has also been used to treat inflammatory bowel disease. Methotrexate has the following chemical structure:

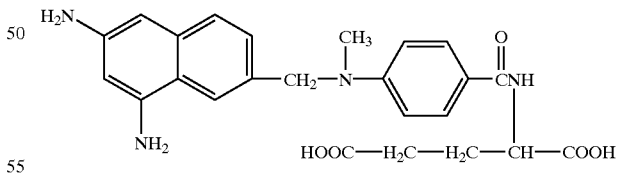

The polypeptide cyclosporine, which has traditionally been given to transplant patients to prevent organ rejection, has also been used to treat inflammatory bowel disease. The use of cyclosporine to treat IBD may be limited, however, by the various side effects associated with this medication. These side effects include high blood pressure, kidney damage, tremors, headaches, seizures, excessive hair growth, excessive gum growth, confusion, coma, and gout.

It is also known to use the absorbable antibiotics metronidazole and ciprofloxacin to treat inflammatory bowel disease.

SUMMARY OF THE INVENTION

According to embodiments of the present invention, compounds are provided having the structure of Formula I:

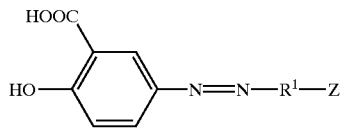

(I)

where $R^1$ is a substituted or unsubstituted phenyl group, and where Z is selected such that a compound, $Z-R^1-NH_2$, formed by cleavage of the azo bond is a non-absorbable antibiotic. Preferably, the compound, $Z-R^1-NH_2$, is a metabolite formed by in vivo cleavage of the azo bond. $R^1$ is preferably an unsubstituted phenyl group. When $R^1$ is a substituted phenyl, it is preferably substituted with lower alkyl.

According to other embodiments of the present invention, compounds are provided having the structure of Formula II:

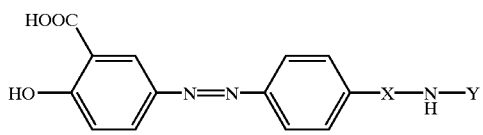

(II)

where X is $-SO_2-$ or $-CO-$ and Y is:

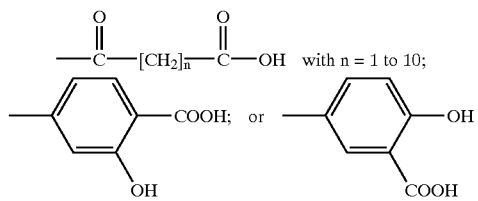

or the esters or pharmaceutically acceptable salts thereof.

Pharmaceutical compositions including compounds according to the present invention in admixture with a pharmaceutical diluent or carrier are also provided, as are methods of utilizing such compounds in the treatment or prophylaxis of various diseases including, but not limited to, inflammatory bowel disease.

DETAILED DESCRIPTION OF THE PREFERRED EMBODIMENTS

Figure 1:
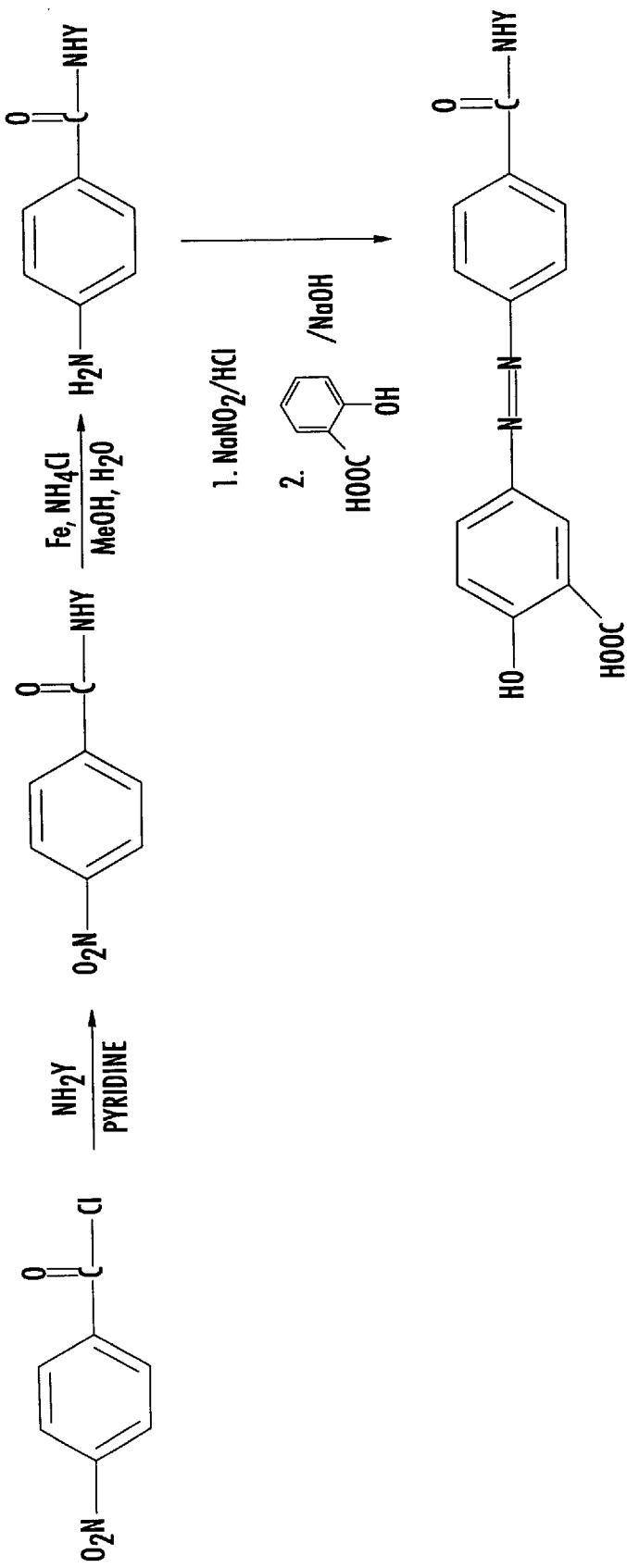
FIG. 1 illustrates a synthesis route for compounds of the present invention.

The invention will now be described with respect to preferred embodiments described herein. It should be appreciated however that these embodiments are for the purpose of illustrating the invention, and are not to be construed as limiting the scope of the invention as defined by the claims.

As used herein, the term "inflammatory bowel disease" includes ulcerative colitis and Crohn's disease.

As used herein, the term "non-absorbable antibiotic" means a compound having anti-bacterial activity, which,
when delivered orally, results in less than 2 percent of the compound being excreted in the urine of the subject, in contrast to the sulfapyridine metabolite resulting from administration of sulfasalzine described above.

According to embodiments of the present invention, compounds are provided having the structure of Formula I:

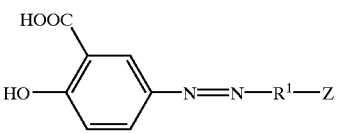

(I)

where $R^1$ is a substituted or unsubstituted phenyl group, and where Z is selected such that a compound, $Z-R^1-NH_2$, formed by cleavage of the azo bond is a non-absorbable antibiotic. Preferably, the compound, $Z-R^1-NH_2$, is a metabolite formed by in vivo cleavage of the azo bond. $R^1$ is preferably an unsubstituted phenyl group. When $R^1$ is a substituted phenyl, it is preferably substituted with lower alkyl.

According to other embodiments of compounds of the present invention, Z is a moiety comprising carbonyl, sulfur, sulfinyl or sulfonyl; and a primary, secondary or tertiary amine. Preferably, Z is a moiety comprising sulfur, sulfinyl or sulfonyl; and a primary, secondary or tertiary amine.

According to yet other embodiments of compounds of the present invention, Z is $-X-V$, where X is carbonyl, sulfur, sulfinyl or sulfonyl; and V is a moiety comprising a primary, secondary or tertiary amine. Preferably, X is sulfur, sulfinyl or sulfonyl. More preferably, X is sulfonyl. In some embodiments, V is $-NH-Y$, where Y is selected from the group consisting of:

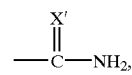

where X" is O or S;

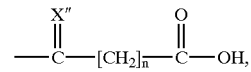

where n=1 to 10, and X"=O or S; and

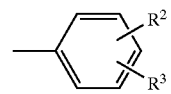

where $R^2$ is hydrogen or hydroxy, and $R^3$ is selected from the group consisting of:

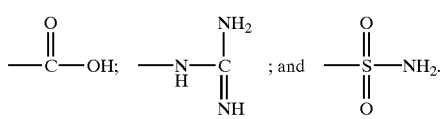

In other embodiments, V is:

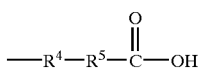

where $R^6$ is substituted or unsubstituted phenyl, and $R^5$ is selected from the group consisting of:

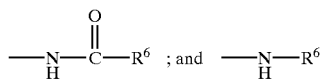

where $R^6$ is a linear or branched alkyl having 1 to 10 carbon atoms. Preferably, $R^4$ is unsubstituted phenyl. Preferably, $R^6$ is a linear or branched alkyl having 1 to 6, 7 or 8 carbon atoms, and, more preferably, $R^6$ is a linear or branched alkyl having 1 or 2 to 3, 4 or 5 carbon atoms.

According to preferred embodiments of the present invention, compounds are provided having the structure of Formula II:

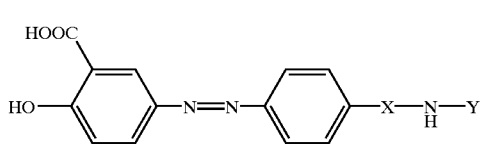

(II)

where X is —$SO_2$— or —CO— and Y is:

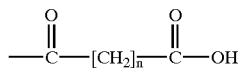

where n is an integer from 1 to 10, is preferably an integer from 1 to 6, and is more preferably an integer from 1 to 3;

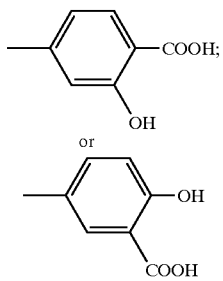

Compounds of the present invention may be utilized for the prophylaxis or treatment of various diseases including, but not limited to, intestinal diseases such as inflammatory bowel disease and traveler's diarrhea; liver diseases such as hepatic encephalopathy, liver failure, end-stage liver disease, cirrhosis, hepatitis, hepatic fibrosis, liver transplantation, and portal hypertension; and diseases that may be treated or prevented by administration of a non-absorbable antibiotic such as bacterial intestinal infections, pseudo membranous colitis, bacterial overgrowth, elostridium difficile infection, salmonella enteritis, shigella infections, yersiniosis, *E. coli*, traveler's diarrhea, gram negative bacterial infections, gram positive bacterial infections, tuberculosis, cryptosporidiosis, and microsporidia infection.

The compounds of the present invention may also be utilized in diagnosis of constituents, conditions, or disease states in biological systems or specimens, as well as for diagnosis purposes in non-physiological systems. Furthermore, the compounds of the present invention may have application in prophylaxis or treatment of condition(s) or disease state(s) in plant systems. By way of example, the compounds of the present invention may have insecticidal, herbicidal, fungicidal, and/or pesticidal efficacy amenable to usage in various plant systems.

Compounds of the present invention preferably break down in the intestinal tract by azo reduction to provide 5-ASA and a non-absorbable antibiotic. For example, according to some embodiments of the present invention, the compounds of Formula II above may breakdown in the intestinal tract to form the metabolic products of Formulae III and IV:

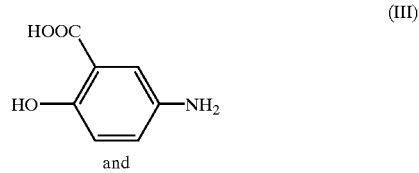

(III)

and

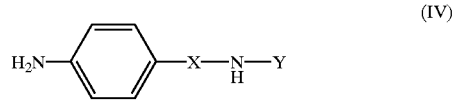

(IV)

where X is —$SO_2$ or —CO— and Y is:

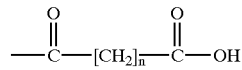

where n is an integer from 1 to 10, is preferably an integer from 1 to 6, and is more preferably a n integer from 1 to 3;

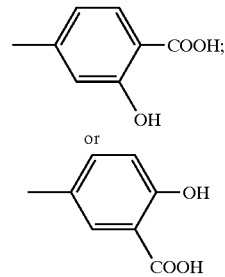

The metabolic product of Formula III preferably possesses anti-inflammatory activity, and more particularly may inhibit prostaglandin synthetase I and II. The metabolic product of Formula IV preferably possesses antibiotic activity and is a non-absorbable antibiotic. Accordingly, compounds of the present invention preferably provide both anti-inflammatory and antibiotic activity, and thus may be useful in treating various diseases, including, but not limited to, intestinal diseases, liver diseases, and diseases that may be treated or prevented by administration of a non-absorbable antibiotic.

In therapeutic usage, the present invention contemplates a method of treating an animal subject having or latently susceptible to such condition(s) or disease state(s) and in need of such treatment, comprising administering to such animal an effective amount of a compound of the present invention that is therapeutically effective for said condition or disease state. Subjects to be treated by the compounds of the present invention include both human and non-human animal (e.g., bird, dog, cat, cow, horse) subjects, and are preferably mammalian subjects, and most preferably human subjects.

Depending on the specific condition or disease state to be combatted, animal subjects may be administered compounds of the present invention at any suitable therapeutically effective and safe dosage, as may readily be determined within the skill of the art, and without undue experimentation. For example, compounds of the present invention may be administered at a dosage between about 0.1 and 100 mg/kg, preferably between about 5 and 90 mg/kg, and more preferably between about 10 and 80 mg/kg.

The compounds of the present invention may be administered perse as well as in the form of pharmaceutically acceptable esters, salts, and other physiologically functional derivatives thereof.

The present invention also contemplates pharmaceutical formulations, both for veterinary and for human medical use, which comprise as the active agent one or more compound(s) of the present invention. In such pharmaceutical and medicament formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and are preferably not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intrauterine administration. Formulations suitable for oral and parenteral administration are preferred, with formulations suitable for oral administration most preferred.

When the active agent is utilized in a formulation comprising a liquid solution, the formulation advantageously may be administered orally or parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously be administered orally. Alternatively, it may be administered bronchially, via nebulization of the powder in a carrier gas, to form a gaseous dispersion of the powder which is inspired by the patient from a breathing circuit comprising a suitable nebulizer device.

The formulations comprising the active agent of the present invention may conveniently be presented in unit dosage forms and may be prepared by any of the methods well-known in the art of pharmacy. Such methods generally include the step of bringing the active ingredient(s) into association with a carrier which constitutes one or more accessory ingredients. Typically, the formulations are prepared by uniformly and intimately bringing the active ingredient(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include, for example, flavorings, suitable preservatives, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of the active compound with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

Accordingly, compounds according to the present invention may be utilized for the prophylaxis or treatment of various diseases, particularly intestinal diseases, and more particularly colonic inflammation diseases such as ulcerative colitis.

Figure 2:
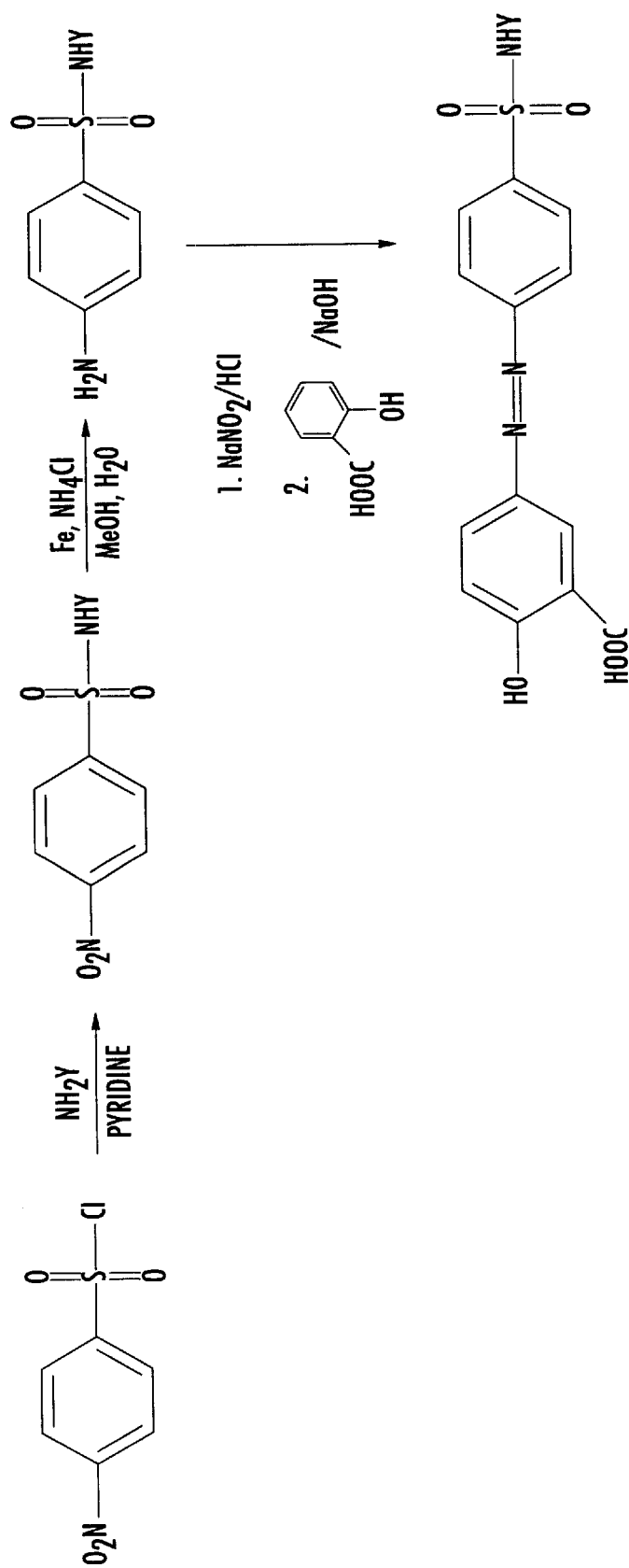
FIG. 2 illustrates a synthesis route for compounds of the present invention.

Compounds of the present invention may be made using known starting materials and reagents as will be understood by those skilled in the art. For example, compounds of the present invention may be synthesized as illustrated in FIGS. 1 and 2, where Y is as described above.

The present invention will now be described with reference to the following examples. It should be appreciated that these examples are for the purposes of illustrating aspects of the present invention, and do not limit the scope of the invention as defined by the claims.

EXAMPLES

Melting points were taken on a Laboratory Devices Mel-Temp II capillary melting point apparatus and are uncorrected. $^1$HNMR spectra were obtained on a Varian Unity 300 MHz spectrometer and chemical shifts (δ) are reported as parts per million (ppm) relative to internal standard tetramethylsilane. Infrared spectra were obtained with a Nicolet Impact 410. Ultraviolet and visible spectra were obtained with a Beckman DU 640i spectrophotometer. Fast atom bombardment (FAB) mass spectroscopy data was obtained by M-Scan Inc. All reagents were used as received from Aldrich Chemical Co.

Examples 1 through 3

Synthesis of 5-[4-(2-Carboxy-Acetylsulfamoyl)-Phenylazo]-2-Hydroxy-Benzoic Acid

Example 1

3-(4-Nitro-Benzenesulfonylamino)-3-Oxo-Propionic Acid Ethyl Ester

A 250-mL flask was charged with 4-nitrobenzenesulfonamide (10.8 g, 53.1 mmol) and sodium hydroxide (2.52 g, 63.1 mmol in 25 mL water). The solution was cooled in an ice bath and ethyl 3-chloro-3-oxobutyrate (6.40 mL, 50.0 mmol) was added dropwise. A precipitate formed, the suspension was allowed to warm to ambient temperature, and stirred for an additional 3 hours. The precipitate was removed by vacuum filtration and the filtrate was extracted with ethyl acetate (3×30 mL). The extractions were combined and dried with $MgSO_4$. The solution was then concentrated under reduced pressure and dried under vacuum. The crude product was a yellow solid with a 57% yield (9.05g): mp 97° C.; $^1$H NMR (DMSO-$d_6$) δ 1.17 (3H, t),3.32 (2H, s), 4.04 (2H, m) 7.71 (1H, s), 8.05 (1H, d, J=9.0 Hz), 8.16 (1H, d, J=8.1 Hz), 8.41 (2H, m); IR (KBr) 2979, 1758, 1690, 1527, 1326, 1207, 1095, 1013, 850, 656 cm$^{-1}$; FAB-MS (NBA) m/z 317 (M+H)$^+$.

Example 2

3-(4-Amino-Benzenesulfonylamino)-3-Oxo-Propionic Acid Ethyl Ester

To a 250-mL oven dried flask, 3-(4-nitro-benzenesulfonylamino)-3-oxo-propionic acid ethyl ester (2.00g, 6.32 mmol), as obtained from the procedure of Example 1, was dissolved in absolute ethyl alcohol (100 mL). Palladium (10 wt. % on activated carbon, 0.20 g, 1.90 mmol) was added and a hydrogen environment was introduced into the flask. The mixture was then stirred at ambient temperature for 3 hours. The crude reaction mixture was filtered through Celite and ethyl alcohol was removed under reduced pressure. The crude product was dried under vacuum overnight resulting in a brown oil (93% yield, 1.68 g): $^1$H NMR (DMSO-$d_6$) δ 1.14 (2H, t), 3.28 (2H, s), 4.07 (2H, m), 6.57 (2H, m), 6.84 (1H, s), 7.44 (1H, d, J=8.1 Hz), 7.52 (1H, d, J=8.1 Hz); JR (KBr) 2979, 1746,1639, 1583, 1370, 1295, 1164, 1026, 857, 669 cm$^{-1}$; FAB-MS (NBA) m/z 287 (M+H)$^+$.

Example 3

5-[4-(2-Carboxy-Acetylsulfamoyl)-Phenylazo]-2-Hydroxy-Benzoic Acid 3-(4-Amino-benzenesulfonylamino)-3-oxo-propionic acid ethyl ester (1.81 g, 6.32 mmol), as obtained from the procedure of Example 2, dissolved in an aqueous solution of HCl (5.5 mL, 36.5–38.0%) and water (3.5 mL) was placed in a 25-mL beaker and cooled to 0° C. in an ice bath. When the solution stabilized at 0° C., sodium nitrite (0.44 g, 6.32 mmol) in water (3 mL) was added dropwise. The temperature was maintained at 0–5° C. and the resulting diazonium salt solution was stirred for 15 minutes.

While the diazonium salt solution stirred, a 50-mL beaker fitted with a thermometer and pH probe (Orion model 420A with Orion semi-micro pH probe) was charged with salicylic acid, sodium salt (1.21 g, 7.59 mmol) dissolved in sodium hydroxide (0.76 g, 19.0 mmol in 6 mL $H_2O$). Using an ice bath, the salicylic acid solution was cooled to 17° C. and the diazonium salt solution was slowly added dropwise. Throughout the addition, the pH was maintained at 13.2–13.3 with the addition of aqueous sodium hydroxide and the temperature was kept at 17–18° C. with the addition of ice. After the addition was complete, the resulting dark red solution was allowed to warm to ambient temperature and stirring was continued for 1.5 h. Using an ice bath, the solution was acidified to pH 2–3 with concentrated HCl (36.5–38.0%). A solid precipitated and was collected by vacuum filtration. The crude product was obtained as a red solid in 4% yield (116 mg): mp 178° C.; $^1$H NMR (DMSO-$d_6$) δ 3.28 (2H, s), 7.13 (1H, d, J=9.0 Hz), 7.47 (1H, m), 7.76 (2H, d, J=6.0 Hz), 7.98 (2H, d, J=6.0 Hz), 8.35 (1H, s); IR (KBr) 3574, 1677, 1577, 1477, 1333, 1138, 1095, 838 cm$^{-1}$; FAB-MS (NBA) m/z 408 (M+H)$^+$, 430 (M+Na)$^+$.

Examples 4 through 6

Synthesis of 5-[4-(4-Carboxy-Butyrylsulfamoyl)-Phenylazo]-2-Hydroxy-Benzoic Acid

Example 4

5-(4-Nitro-Benzesulfonylamino)-5-Oxo-Pentanoic Acid Metbyl Ester

A 250-mL, 3-neck flask fitted with a condenser and stir bar was charged with 4-nitrobenzenesulfonamide (4.02 g, 19.8 mmol) and anhydrous pyridine (60 mL). The solution was heated to reflux using an oil bath and methyl 5-chloro-5-oxovalerate (3.28 mL, 23.7 mmol) was added dropwise. The solution refluxed for 3 hours, cooled to ambient temperature and continued stirring for 20 hours. The solution was acidified with HCl (50 mL, 36.5–38%) in water (150 mL) to pH 1–2 upon which a precipitate formed. The crude product was obtained by suction filtration as a brown solid (6.59 g): mp 114° C.; $^1$H NMR (DMSO-$d_6$): δ 1.62 (2H, m), 2.19(2H, m), 2.28 (2H, m) 3.52 (3H, s), 8.15 (2H, d, J=9.0 Hz), 8.42 (2H, d, J=9.0 Hz); IR (KBr) 3205, 1727, 1690, 1527, 1420, 1352, 1319, 1170, 1020, 838, 744 cm$^{-1}$; negative FAB-MS (NBA) m/z 329 (M)$^-$.

Example 5

5-(4-Amino-Benzenesulfonylamino)-5-Oxo-Pentanoic Acid Methyl Ester

A 250-mL, 3-neck flask fitted with a condenser was charged with 5-(4-nitro-benzesulfonylamino)-5-oxo-pentanoic acid methyl ester (6.00 g, 18.2 mmol), as obtained from the procedure of Example 4, dissolved in methanol (60 mL). A solution of ammonium chloride (5.64 g, 105 mmol) in water (60 mL) was added along with iron (3.55 g, 63.6 mmol, 325 mesh powder). The solution refluxed for 15 hours, cooled to ambient temperature, and was filtered through Celite. The solvent was removed under reduced pressure and methanol (200 mL) was added. The solution was filtered and concentrated under reduced pressure. The crude product was obtained as an orange solid in 91% yield (4.95 g): mp>260° C.; IR (KBr) 3117, 2823, 1746, 1596, 1395, 1157 cm$^{-1}$; FAB-MS (NBA) m/z 301 (M)$^+$.

Example 6

5-[4-(4-Carboxy-Butyrylsulfoamoyl)-Phenylazo]-2-Hydroxy-Benzoic Acid 5-(4-Amino-benzenesulfonylamino)-5-oxo-pentanoic acid methyl ester (4.00 g, 13.3 mmol), as obtained from the procedure of Example 5, dissolved in an aqueous solution of HCl (13 mL, 36.5–38%) and water (8 mL) was placed in a 100-mL beaker and cooled to 0° C. in an ice bath. When the solution stabilized at 0° C., sodium nitrite (1.60 g. 39.9 mmol) in water (5 mL) was added dropwise. The temperature was maintained at 0–5° C. and the resulting diazonium salt solution stirred for 20 minutes.

While the diazonium salt solution stirred, a 400-mL beaker fitted with a thermometer and pH probe (Orion model 420A with Orion semimicro pH probe) was charged with salicylic acid, sodium salt (2.56 g. 16.0 mmol) dissolved in sodium hydroxide (1.60 g, 39.9 mmol) in water (5 mL) and sodium carbonate (2.50 g. 23.6 mmol) in water (5 mL). Using an ice bath, the salicylic acid solution was cooled to 17° C. and the diazonium salt solution was slowly added in 3–4 mL portions. Throughout the addition, the pH was maintained at 13.2–13.3 with the addition of aqueous sodium hydroxide and the temperature was kept at 17–18° C. with the addition of ice. After the addition was complete, the resulting solution was allowed to warm to ambient temperature and stirring was continued for 1 hour. Using an ice bath, the solution was acidified to pH 1–2 with concentrated HCl (100 mL, 36.5–38%) in water (250 mL). A solid precipitated and was collected by suction filtration. The crude product was obtained as an orange solid in 6% yield (36.5 mg): mp 192° C.; $^1$H NMR (DMSO-d$_6$): δ 1.62 (2H, m), 2.13 (2H, m), 2.28 (2H, m), 7.17 (1H, d, J=7.8 Hz), 8.02 (3H, d, J=6.0 Hz), 8.10 (2H, d, J=7.8 Hz), 8.37 (1H, s); IR (KBr) 3092, 1677, 1441, 1169, 1143, 1070,851, 659 cm$^{-1}$; FAB-MS (NBA) m/z 434 (M)$^+$.

Examples 7 through 9

Synthesis of 5-[4-(3-Carboxy-Propionylsulfamoyl)-Phenylazo]-2-Hydroxy-Benzoic Acid

Example 7

4-(4-Nitro-Benzenesulfonylamino)-4-Oxo-Butyric Acid Methyl Ester

A 500-mL, 3-neck flask fitted with a condenser was charged with 4-nitrobenzenesulfonamide (8.03 g, 39.7 mmol) and anhydrous pyridine (150 mL). The solution was heated to reflux using an oil bath and methyl 4-chloro-4-oxobutyrate (5.90 mL, 47.9 mmol) was added dropwise. The solution refluxed for 17 hours, cooled to ambient temperature, and was further cooled to 0–5° C. using an ice bath. The solution was acidified with conc. HCl (~50 mL, 36.5–38%) to pH 3 and poured into a beaker containing ~600 grams of ice upon which a precipitate formed. The crude product was obtained by suction filtration as a brown solid in 92% yield (11.5 g): mp 156° C.; $^1$H NMR (DMSO-d$_6$) δ 2.43 (2H, m), 2.50 (2H, m), 3.47 (3H, s), 8.14 (2H, d, J=9.0 Hz), 8.41 (2H, d, J=9.0 Hz); IR (KBr) 3211, 1739, 1706, 1533, 1434, 1348, 1162 cm$^{-1}$; FAB-MS (NBA) miz 317 (M+H)$^+$.

Example 8

4-(4-Amino-Benzesulfonylamino)4-Oxo-Butyric Acid Methyl Ester

To a 500-mL, 2-neck flask fitted with an overhead stirrer and condenser, 4-(4-nitro-benzenesulfonylamino)-4-oxo-butyric acid methyl ester (10.0 g. 31.6 mmol), as obtained by the procedure of Example 7, was dissolved in methanol (100 mL). A solution of ammonium chloride (9.82 g. 184 mmol) in water (100 mL) was added along with iron (6.19 g, 11 mmol, 325 mesh powder). The solution was refluxed for 5.5 hours, cooled to ambient temperature and filtered through Celite. The solvent was removed under reduced pressure and methanol (400 mL) was added. The solution was filtered and concentrated under reduced pressure. The crude product was obtained as a brown solid (9.58 g): mp>260° C.; $^1$H NMR (DMSO-d$_6$) δ 2.38 (2H, m) 2.48 (2H, m), 3.46(3H, s), 6.56(2H, d, J=8.4 Hz), 7.44 (2H, d, J=8.4 Hz); IR (KBr) 3490, 3386, 3107, 1739, 1697, 1624, 1587, 1435, 1314, 1138, 1083, 980, 840 cm$^{-1}$ FAB-MS (NBA) m/z 287 (M+H)$^+$.

Example 9

5-[4-(3-Carboxy-Propionylsulfamoyl)-Phenylazo]-2-Hydroxy-Benzoic Acid 4-(4-Amino-benzenesulfonylamino)-4-oxo-butyric acid methyl ester (11.5 g. 40.2 mmol), as prepared from the procedure of Example 8, dissolved in an aqueous solution of HCL (35 mL, 36.5–38.0%) and water (25 mL) was placed in a 500-mL beaker and cooled to 0° C. in an ice bath. When the solution stabilized at 0° C., sodium nitrite (2.77 g, 40.2 mmol) in water (15 mL) was added slowly in 5 mL portions. The temperature was maintained at 0–5° C. and the resulting diazonium salt solution was stirred for 15 minutes.

While the diazonium salt solution stirred, a 1L beaker fitted with a thermometer and pH probe (Orion model 420A with Orion semimicro pH probe) was charged with salicylic acid, sodium salt (6.44 g, 40.2 mmol) dissolved in sodium hydroxide (4.83 g, 121 mmol in 15 mL H$_2$O) and sodium carbonate (7.54 g, 71.2 mmol in 15 mL H$_2$O). Using an ice bath, the salicylic acid solution was cooled to 17° C. and the diazonium salt solution was slowly added in 20 mL portions. Throughout the addition, the pH was maintained at 13.2–13.3 with the addition of aqueous sodium hydroxide and the temperature was kept at 17–18° C. with the addition of ice. After the addition was complete, the resulting dark red solution was allowed to warm to ambient temperature and stirring was continued for an additional 30 minutes. Using an ice bath, the solution was acidified to pH 2–3 with concentrated HCl (300 mL, 36.5–38.0%) in water (500 mL). A solid precipitated and was collected by suction filtration. The crude product was obtained as an orange solid in 36% yield (6.24 g): mp 192° C., $^1$H NMR (DMSO-d$_6$) δ 2.37 (2H, m), 2.46 (2H, m), 7.14 (1H, d, J=9.0 Hz), 7.97 (1H, d, J=8.4 Hz), 8.00 (2H, d, J=8.4 Hz), 8.06 (2H, d, J=8.4 Hz), (1H, s); IR(KBr) 3596, 3536, 3178,1713, 1680, 1573, 1448, 1334, 1182, 1123, 1063, 851, 791, 612 cm$^{-1}$; UV-Vis (MeOH) λ$_{max}$=353 nm, ε=23,400 mol$^{-1}$ cm$^{-1}$ L; FAB-MS (NBA) m/z 420 (M)$^-$.

Example 10

Metabolism of 5-[4-(3-Carboxy-Propionylsulfamoyl)-Phenylazo]-2-Hydroxy-Benzoic Acid (1) Following Oral Delivery 5-[4-(3-Carboxy-propionylsulfamoyl)-phenylazo]-2-hydroxy-benzoic acid (1), a compound of the present invention, and sulfasalazine (used as a control; not part of the present invention) were orally dosed to rats. The degradation and the generation of their metabolites after the oral dosing were measured to be able to confirm that (1) undergoes bacterial azo reduction and yields its metabolites, 5-aminosalicylic acid (5-ASA) and C4 sulfanomide.

This experiment was performed to confirm that (1) undergoes a bacterial reduction process and yields its metabolites in in-vivo metabolism. The quantification of its metabolites was also carried out. Sulfasalazine was used as a control since the same azo bond cleavage by bacteria occurs with it, which results in 5-aminosalicylic acid and sulfapyridine as its metabolites. (1) was degraded and its metabolites were produced as expected.

A total of 7 rats were used for the experiment and methylcellulose was used as a vehicle. The dosage amount was 100 mg/kg per rat. Three rats were dosed with (1) and the other three rats were dosed with sulfasalazine. One rat was used as a control and dosed with methylcellulose. Both urine and feces were collected over 2 days and analyzed by BPLC.

Urine was collected each day and 300 µL of aliquot from each sample was centrifuged for 10 minutes at 5000 g. 80 µL of supernatant was injected for analysis. Feces was also collected, each day and homogenized with a 1:1 mixture of water and acetonitrile. This mixture was then centrifuged for 20 minutes at 5000 g. 80 µL of supernatant was injected for analysis.

A Waters 2690 HPLC was used for sample analysis as follows:
Mobile phase programming: Gradient
Mobile phase: A=Water+0.1% TFA B=Acetonitrile+0.1% TFA
Flow rate: 1 ML/min.
Column: Phenomenex Max RP, 80 Å, 4.6 mm×250 mm
PDA settings: Collected spectrum: 210–400nm Extracted chromatogram: 280 and/or other
Run time/sample: Approximately 50 min.

| Time | Flow (mL/minute) | % Mobile Phase A | % Mobile Phase B |
|---|---|---|---|
| — | 1 | 100 | 0 |
| 40 | 1 | 50 | 50 |
| 43 | 1 | 5 | 95 |
| 44 | 1 | 95 | 5 |
| 50 | 1 | 95 | 5 |

For urine, only a very small amount of (1) was detected from 2 days collection and none of its metabolites were detected. For feces, (1) was not detected, but acetylated 5-ASA and C4 sulfanomide were detected from day 1 collection. No compounds were detected from day 2 collection. Sulfasalazine was also degraded, but only one rat showed the generation of sulfapyridine. Most rats showed acetylated 5-ASA from day 1 collection. No compounds were detected from day 2 collection. The results from this study show that both (1) and sulfasalazine undergo azo reduction.

The foregoing is illustrative of the present invention, and is not to be construed as limiting thereof. The invention is defined by the following claims, with equivalents of the claims to be included therein.

That which is claimed is:
1. A compound of the formula:

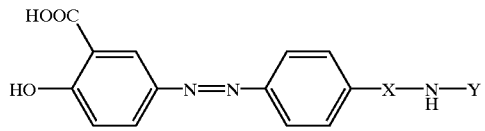

where X is —SO$_2$— or —CO— and Y is:

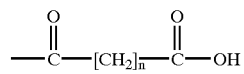

where n is an integer from 1 to 3;

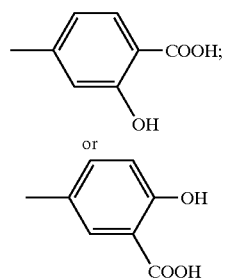

or an ester or pharmacologically acceptable salt thereof.

2. The compound according to claim 1, wherein X is —SO$_2$— and Y is:

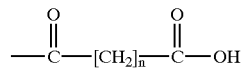

where n is an integer from 1 to 3.

3. The compound according to claim 1, 5-[4-(2-carboxyacetylsulfamnoyl)-phenylazo]-2-hydroxy-benzoic acid.

4. The compound according to claim 1, 5-[4-(4-carboxybutyrylsulfoamoyl)-phenylazo]-2-hydroxy-benzoic acid.

5. The compound according to claim 1, 5-[4-(3-carboxypropionylsulfamoyl)-phenylazo]-2-hydroxy-benzoic acid.

6. A pharmaceutical composition for the treatment of an intestinal disease in subjects in need of such treatment, comprising an amount effective to treat the intestinal bowel disease of a compound of the formula:

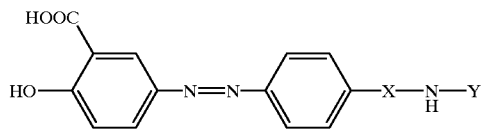

where X is —SO$_2$— or —CO— and Y is:

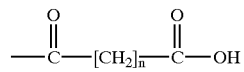

where n is an integer from 1 to 3;

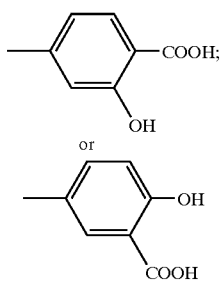

or or an ester or pharmacologically acceptable salt thereof, in admixture with a solid or liquid pharmaceutical diluent or carrier.

7. The pharmaceutical composition according to claim 6, wherein X is —SO$_2$— and Y is:

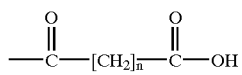

where n is an integer from 1 to 3.

8. The pharmaceutical composition according to claim 6, wherein the compound is 5-[4-(2-carboxy-acetylsulfamoyl)-phenylazo]-2-hydroxy-benzoic acid.

9. The pharmaceutical composition according to claim 6, wherein the compound is 5-[4-(4-carboxy-butyrylsulfoamoyl)-phenylazo]-2-hydroxy-benzoic acid.

10. The pharmaceutical composition according to claim 6, wherein the compound is 5-[4(3-carboxy-propionylsulfamoyl)-phenylazo]-2-hydroxy-benzoic acid.

11. A method of treating an intestinal disease in a subject in need of such treatment, said method comprising administering to the subject an amount effective to treat the intestinal disease of a compound having the following formula:

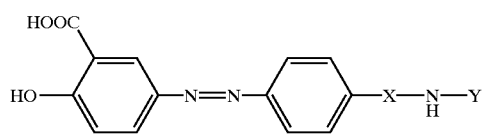

where X is —SO$_2$— or —CO— and Y is:

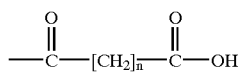

where n is an integer from 1 to 3;

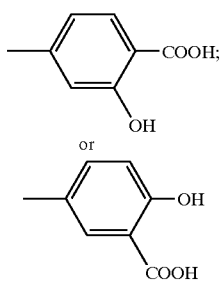

or an ester or pharmacologically acceptable salt thereof.

12. The method according to claim 11, wherein X is —SO$_2$— and Y is:

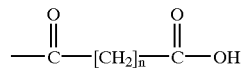

where n is an integer from 1 to 3.

13. The method according to claim 11, wherein the compound is 5-[4-(2-carboxy-acetylsulfamoyl)-phenylazo]-2-hydroxy-benzoic acid.

14. The method according to claim 11, wherein the compound is 5-[4-(4-carboxy-butyrylsulfoamoyl)-phenylazo]-2-hydroxy-benzoic acid.

15. The method according to claim 11, wherein the compound is 5-[4-(3-carboxy-propionylsulfamoyl)-phenylazo]-2-hydroxy-benzoic acid.

16. The method according to claim 11, wherein the intestinal disease is Crohn's disease.

17. The method according to claim 11, wherein the intestinal disease is ulcerative colitis.

18. The method according to claim 11, wherein the intestinal disease is traveler's diarrhea.

19. A pharmaceutical composition for the treatment of a liver disease in subjects in need of such treatment, comprising an amount effective to treat the liver disease of a compound of the formula:

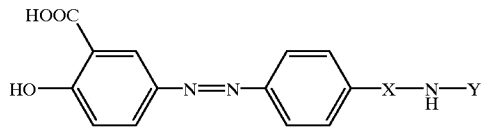

where X is —SO$_2$— or —CO— Y is:

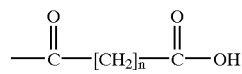

where n is an interger from 1 to 3;

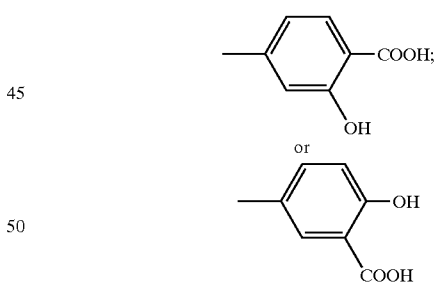

or an ester or pharmacologically acceptable salt thereof, in admixture with a solid or liquid pharmaceutical diluent or carrier.

20. The pharmaceutical composition according to claim 19, wherein X is —SO$_2$— and Y is:

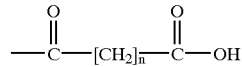

where n is an interger from 1 to 3.

21. The pharmaceutical composition according to claim 19, wherein the compound is 5-[4-(2-carboxyl-acetylsulfamoyl)-phenylazo]-2-hydroxy-benzoic acid.

22. The pharmaceutical composition according to claim 19, wherein the compound is 5-[4-(4-carboxy-butyrylsulfoamoyl)-phenylazo]-2-hydroxy-benzoic acid.

23. The pharmaceutical composition according to claim 19, wherein the compound is 5-[4-(3-carboxy-propionylsulfamoyl)-phenylazo]-2-hydroxy-benzoic acid.

24. A method of treating a liver disease in a subject in need of such treatment, said method comprising administering to the subject an amount effective to treat the liver disease of a compound having the following formula:

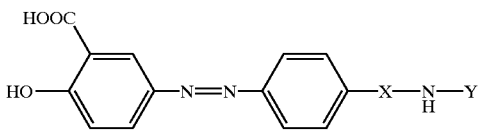

where X is —$SO_2$— or —CO— and Y is:

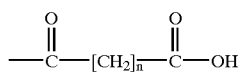

where n is an integer from 1 to 3;

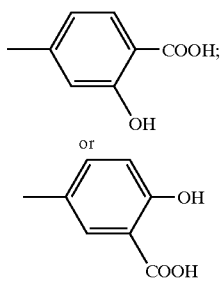

or an ester or pharmacologically acceptable salt thereof.

25. The method according to claim 24, wherein X is —$SO_2$— and Y is:

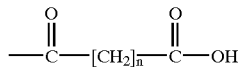

where n is an integer from 1 to 3.

26. The method according to claim 24, wherein the compound is 5-[4-(2-carboxy-acetylsulfamoyl)-phenylazo]-2-hydroxy-benzoic acid.

27. The method according to claim 24, wherein the compound is 5-[4-(4-carboxybutyrylsulfoamoyl)-phenylazo]-2-hydroxy-benzoic acid.

28. The method according to claim 24, wherein the compound is 5-[4-(3-carboxy-propionylsulfamoyl)-phenylazo]-2-hydroxy-benzoic acid.

29. The method according to claim 24, wherein the liver disease is hepatic encephalopathy.

30. A compound of the formula:

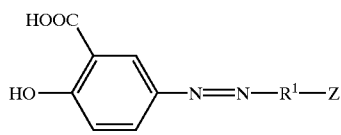

(I)

where $R^1$ is a substituted or unsubstituted phenyl group, and where Z is selected such that a compound, Z-$R^1$-$NH_2$, formed by cleavage of the azo bond is a non-absorbable antibiotic;

or an ester or pharmacologically acceptable salt of the compound of Formula I.

31. The compound according to claim 30, wherein Z is a moiety comprising carbonyl, sulfur, sulfinyl or sulfonyl; and a primary, secondary or tertiary amine.

32. The compound according to claim 30, wherein Z is a moiety comprising sulfur, sulfinyl or sulfonyl; and a primary, secondary or tertiary amine.

33. The compound according to claim 30, wherein Z is —X—V, where X is carbonyl, sulfur, sulfinyl or sulfonyl; and V is a moiety comprising a primary, secondary or tertiary amine.

34. The compound according to claim 33, wherein X is sulfur, sulfinyl or sulfonyl.

35. The compound according to claim 33, wherein V is —NH—Y, where Y is selected from the group consisting of:

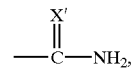

where X' is O or S;

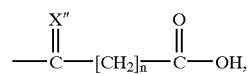

where n=1 to 10, and X'=O or S; and

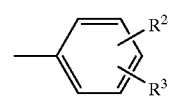

where $R^2$ is hydrogen or hydroxy, and $R^3$ is selected from the group consisting of:

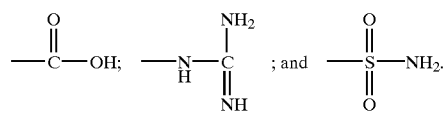

36. The compound according to claim 33, wherein V is:

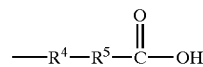

where $R^4$ is substituted or unsubstituted phenyl, and $R^5$ is selected from the group consisting of:

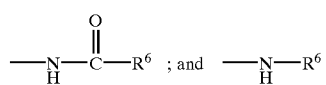

where $R^6$ is a linear or branched alkyl having 1 to 10 carbon atoms.

37. The compound according to claim 36, wherein $R^4$ is an unsubstituted phenyl group.

38. The compound according to claim 36, wherein $R^6$ is a linear or branched alkyl having 1 to 4 carbon atoms.

39. A pharmaceutical composition for the treatment of a disease that is treatable by a non-absorbable antibiotic in subjects in need of such treatment, comprising an amount effective to treat the disease of a compound of the formula:

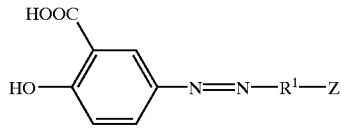
(I)

where $R^1$ is a substituted or unsubstituted phenyl group, and where Z is selected such that a compound, $Z-R^1-NH_2$, formed by cleavage of the azo bond is a non-absorbable antibiotic; or an ester or pharmacologically acceptable salt of the compound of Formula I, in admixture with a solid or liquid pharmaceutical diluent or carrier.

40. The pharmaceutical composition according to claim 39, wherein Z is a moiety comprising carbonyl, sulfur, sulfinyl or sulfonyl; and a primary, secondary or tertiary amine.

41. The pharmaceutical composition according to claim 39, wherein Z is a moiety comprising sulfur, sulfinyl or sulfonyl; and a primary, secondary or tertiary amine.

42. The pharmaceutical composition according to claim 39, wherein Z is —X—V, where X is carbonyl, sulfur, sulfinyl or sulfonyl; and V is a moiety comprising a primary, secondary or tertiary amine.

43. The pharmaceutical composition according to claim 42, wherein X is sulfur, sulfinyl or sulfonyl.

44. The pharmaceutical composition according to claim 42, wherein V is —NH—Y, where Y is selected from the group consisting of:

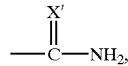

where X' is O or S;

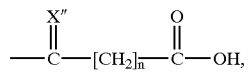

where n=1 to 10, and X"=O or S; and

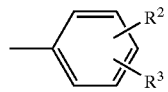

where $R^2$ is hydrogen or hydroxy, and $R^3$ is selected from the group consisting of:

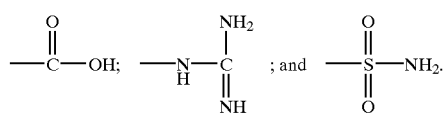

45. The pharmaceutical composition according to claim 42, wherein V is:

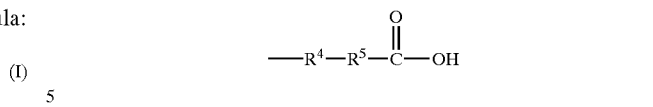

where $R^1$ is substituted or unsubstituted phenyl, and $R^5$ is selected from the group consisting of:

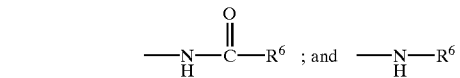

where $R^6$ is a linear or branched alkyl having 1 to 10 carbon atoms.

46. The pharmaceutical composition according to claim 45, wherein $R^4$ is an unsubstituted phenyl group.

47. The pharmaceutical composition according to claim 45, wherein $R^6$ is a linear or branched alkyl having 1 to 4 carbon atoms.

48. A method of treating a disease treatable by a non-absorbable antibiotic in a subject in need of such treatment, said method comprising administering to the subject an amount effective to treat the disease of a compound having the following formula:

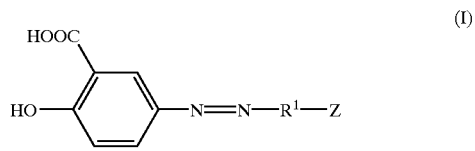
(I)

where $R^1$ is a substituted or unsubstituted phenyl group, and where Z is selected such that a compound, Z-R-$NH_2$, formed by cleavage of the azo bond is a non-absorbable antibiotic;

or an ester or pharmacologically acceptable salt of the compound of Formula I.

49. The method according to claim 48, wherein Z is a moiety comprising carbonyl, sulfur, sulfinyl or sulfonyl; and a primary, secondary or tertiary amine.

50. The method according to claim 48, wherein Z is a moiety comprising sulfur, sulfinyl or sulfonyl; and a primary, secondary or tertiary amine.

51. The method according to claim 48, wherein Z is —X—V, where X is carbonyl, sulfur, sulfinyl or sulfonyl; and V is a moiety comprising a primary, secondary or tertiary amine.

52. The method according to claim 51, wherein X is sulfur, sulfinyl or sulfonyl.

53. The method according to claim 51, wherein V is —NH—Y, where Y is selected from the group consisting of:

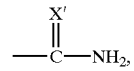

where X' is O or S;

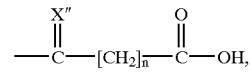

where n=1 to 10, and X"=O or S; and

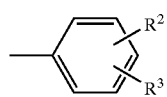

where $R^2$ is hydrogen or hydroxy, and $R^3$ is selected from the group consisting of:

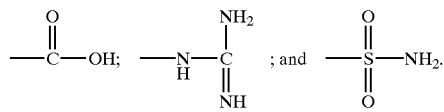

54. The method according to claim 51, wherein V is:

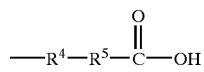

where $R^4$ is substituted or unsubstituted phenyl, and $R^5$ is selected from the group consisting of:

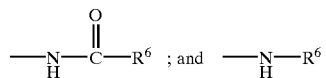

where $R^6$ is a linear or branched alkyl having 1 to 10 carbon atoms.

55. The method according to claim 54, wherein $R^4$ is an unsubstituted phenyl group.

56. The method according to claim 54, wherein $R^6$ is a linear or branched alkyl having 1 to 4 carbon atoms.

57. The method according to claim 48, wherein the disease is Crohn's disease.

58. The method according to claim 48, wherein the disease is ulcerative colitis.

59. The method according to claim 48, wherein the disease is traveler's diarrhea.

60. The method according to claim 48, wherein the disease is hepatic encephalopathy.

* * * * *

UNITED STATES PATENT AND TRADEMARK OFFICE
CERTIFICATE OF CORRECTION

PATENT NO.    : 6,458,776 B1                                            Page 1 of 1
DATED         : October 1, 2002
INVENTOR(S)   : Ekwuribe et al.

It is certified that error appears in the above-identified patent and that said Letters Patent is hereby corrected as shown below:

Column 13,
Line 23, should read -- HPLC. --

Column 14,
Line 43, should read -- acetylsulfamoyl-phenylazo]-2-hydroxy-benzoic acid. --

Column 15,
Line 33, should read -- wherein the compound is 5-[4-(3-carboxy- --

Column 16,
Line 64, should read -- where n is an integer from 1 to 3. --
Line 66, should read -- 19, wherein the compound is 5-[4(2-carboxy- --

Column 17,
Line 50, should read -- compound is 5-[4-(4-carboxy-butyrylsulfoamoyl)- --

Column 18,
Line 30, should read -- where n=1 to 10, and X"=O or S; and --

Column 20,
Line 6, should read -- where $R^4$ is substituted or unsubstituted phenyl, and $R^5$ is --
Line 36, should read -- and where Z is selected such that a compound, $Z-R^1$- --

Signed and Sealed this

First Day of July, 2003

JAMES E. ROGAN
*Director of the United States Patent and Trademark Office*